United States Patent
Yang

(10) Patent No.: US 12,403,247 B2
(45) Date of Patent: Sep. 2, 2025

(54) DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 928 days.

(21) Appl. No.: 17/432,096

(22) PCT Filed: May 17, 2019

(86) PCT No.: PCT/CN2019/087342
§ 371 (c)(1),
(2) Date: Aug. 19, 2021

(87) PCT Pub. No.: WO2020/232565
PCT Pub. Date: Nov. 26, 2020

(65) Prior Publication Data
US 2022/0339763 A1    Oct. 27, 2022

(51) Int. Cl.
*A61M 5/142*    (2006.01)
*A61B 5/00*    (2006.01)
(Continued)

(52) U.S. Cl.
CPC ....... *A61M 5/14248* (2013.01); *A61B 5/4839* (2013.01); *A61M 5/14216* (2013.01);
(Continued)

(58) Field of Classification Search
CPC ...... A61M 2005/14533; A61M 5/3156; A61M 2005/14506; A61M 5/31561;
(Continued)

(56) References Cited

U.S. PATENT DOCUMENTS

2003/0199824 A1* 10/2003 Mahoney ............ A61M 5/1452
604/155
2003/0236498 A1* 12/2003 Gross ................ A61M 5/14216
604/141
(Continued)

FOREIGN PATENT DOCUMENTS

CN    101208515    6/2008
CN    102600526    7/2012
(Continued)

OTHER PUBLICATIONS

"Search Report of Europe Counterpart Application", issued on Nov. 10, 2022, pp. 1-8.
"International Search Report (Form PCT/ISA/210) of PCT/CN2019/087342," mailed on Sep. 2, 2019, with English translation thereof, pp. 1-4.

*Primary Examiner* — Courtney B Fredrickson
*Assistant Examiner* — Kayla M. Turkowski
(74) *Attorney, Agent, or Firm* — JCIP GLOBAL INC.

(57) ABSTRACT

This invention discloses a drug infusion device, including: a drug storage unit; a piston and a driving wheel respectively connected with a screw, the driving wheel drives the screw to move by rotation, the piston is arranged in the drug storage unit, the screw advances the piston to move; a driving unit cooperating with the driving wheel, the driving unit includes more than two driving arms, the driving unit, through the multiple pivoting movement modes, drives driving arms to perform tooth number adjustable driving on the driving wheel for increment-adjustable infusion; and a power unit connected to the driving unit, the power unit exerts a force on the driving unit to lead the driving unit to perform a plurality of pivot steps. More than two driving arms are stalled on the driving unit, thereby achieving multi-level engagement on the driving wheel, and finally achieving the purpose of increment-adjustable infusion.

13 Claims, 7 Drawing Sheets

(51) Int. Cl.
  *A61M 5/145* (2006.01)
  *A61M 5/158* (2006.01)
  *A61M 5/168* (2006.01)
  *A61M 5/172* (2006.01)
  *A61M 5/36* (2006.01)
  *B25B 13/46* (2006.01)
  *B25B 21/00* (2006.01)
  *B25B 23/00* (2006.01)

(52) U.S. Cl.
  CPC .......... *A61M 5/1452* (2013.01); *A61M 5/158* (2013.01); *A61M 5/1684* (2013.01); *A61M 5/16877* (2013.01); *A61M 5/172* (2013.01); *A61M 5/36* (2013.01); *B25B 13/463* (2013.01); *B25B 21/005* (2013.01); *A61B 2560/0209* (2013.01); *A61B 2562/043* (2013.01); *A61M 2005/14208* (2013.01); *A61M 2005/14252* (2013.01); *A61M 2005/14268* (2013.01); *A61M 2005/14533* (2013.01); *A61M 2205/3317* (2013.01); *A61M 2205/3576* (2013.01); *A61M 2205/50* (2013.01); *B25B 23/0078* (2013.01)

(58) Field of Classification Search
  CPC .......... A61M 5/31548; A61M 5/31556; B25B 21/005; B25B 23/0078
  See application file for complete search history.

(56) References Cited

U.S. PATENT DOCUMENTS

| | | | |
|---|---|---|---|
| 2004/0153032 | A1 | 8/2004 | Garribotto et al. |
| 2005/0238507 | A1* | 10/2005 | Dilanni .................. F04B 9/08 417/415 |
| 2019/0117881 | A1 | 4/2019 | Yang |

FOREIGN PATENT DOCUMENTS

| | | |
|---|---|---|
| CN | 106999670 | 8/2017 |
| CN | 207627685 | 7/2018 |
| CN | 208049137 | 11/2018 |
| CN | 108939203 | 12/2018 |
| WO | 2014166889 | 10/2014 |

* cited by examiner

DRUG INFUSION DEVICE

CROSS-REFERENCE TO RELATED APPLICATION

This application is a 371 of international application of PCT application serial no. PCT/CN2019/087342, filed on May 17, 2019. The entirety of the above mentioned patent application is hereby incorporated by reference herein and made a part of this specification.

BACKGROUND

Technical Field

The present invention mainly relates to the field of medical instruments, in particular to a drug infusion device.

Description of Related Art

A drug infusion device is a medical device that achieves treatment of a patient's physiological condition by continuously injecting a drug into a patient. Drug infusion devices are widely used for the treatment of diabetes, allowing required doses of insulin to be continuously infused into the subcutaneous tissue of the patient's body, thereby simulating the secretion function of the pancreas, thereby keeping the patient's blood sugar stable. The drug fluid is usually stored inside the infusion pump. The existing drug infusion device usually attaches the pump body directly to the patient's body through a medical adhesive tape, and the patient operates a remote device to control infusion.

In the case of drug infusion, the current infusion devices can only operate with one level of increment, the infusion process cannot be flexibly controlled, and the infusion efficiency is relatively low. Moreover, the minimum dose that can be infused each time is relatively large, which can cause the concentration of some substance(s) in a patient's body fluid to fluctuate greatly under the control of the infused drug, and cannot achieve the purpose of more accurately controlling the concentration of that substance(s).

Therefore, there is a need in the prior art for a drug infusion device that can flexibly control a drug infusion process and improve drug infusion efficiency.

SUMMARY

The embodiment of the invention discloses a drug infusion device, which is provided with more than two driving arms on the driving unit, thereby realizing tooth number adjustable driving on the driving wheel, and finally achieving the purpose of increment-adjustable infusion and more flexible control. The multi-mode driving improves the efficiency of the infusion.

The invention discloses a drug infusion device, including: a drug storage unit; a piston and a driving wheel respectively connected with a screw, the driving wheel drives the screw movement by rotation, the piston is arranged in the drug storage unit, the screw advances the piston to move; a driving unit cooperating with the driving wheel, the driving unit includes more than two driving arms, the driving unit, through the its own adjustable movement, drives driving arms to rotate the driving wheel by an optional number of gear teeth, resulting in increment-adjustable infusion; and a power unit connected to the driving unit, the power unit exerts a force on the driving unit to lead the driving unit to perform adjustable pivoting movements.

According to an aspect of the invention, the adjustable pivoting movements of the driving unit includes: after pivoting by an optional number of degrees in one direction in a single time, the driving unit starts pivoting by an optional number of degrees in another direction until the end of the pivoting in this direction, the driving unit completes pivoting in both directions to drive the driving wheels to rotate by an optional number of gear teeth.

According to an aspect of the invention, the driving wheel includes a plurality of sub-wheels, the circumferential surface of the sub-wheel being provided with gear teeth, and the driving arms drive the driving wheel by engaging gear teeth.

According to an aspect of the invention, a plurality of driving arms are respectively installed on both sides of the driving unit.

According to an aspect of the invention, when driving arms on one side of the driving unit engage the gear teeth, the lines representing the engaging directions of the plurality of driving arms on this side intersect each other.

According to an aspect of the invention, two driving arms are installed on each side of the driving unit, and two driving arms on the same side of the driving unit are installed up and down, or are installed left and right.

According to an aspect of the invention, the two driving arms on the same side of the driving unit are installed up and down, and when driving arms on one side of the driving unit engage the gear teeth, the angle between the two driving arms on the driving direction is $\alpha$, $0° \leq \alpha \leq 7°$.

According to an aspect of the invention, $3.1° \leq \alpha \leq 4.1°$.

According to an aspect of the invention, $\alpha = 3.5°$.

According to an aspect of the invention, the horizontal distance between the driving ends of the two driving arms on one side of the driving unit is h, the pitch of the gear teeth is s, $0.1 \text{ s} \leq h \leq 2.5 \text{ s}$.

According to an aspect of the invention, $0.5 \text{ s} \leq h \leq 1.5 \text{ s}$.

According to an aspect of the invention, the gear teeth are ratchet teeth, and during the whole process of the driving unit pivoting in one direction, the driving unit alternately pivots and stalls in an adjustable way to drive driving arms to alternately engage and stop engaging the ratchet teeth, so that the driving wheel alternately rotates and stops rotation to realize tooth number adjustable rotation.

According to an aspect of the invention, when the driving unit drives the driving wheel, at least one of the driving arms on the side on which the driving force is applied engages the gear teeth, and the driving arms on the other side of the driving unit does not apply a force to the gear teeth to rotate the driving wheel.

According to an aspect of the invention, the plurality of movement modes of the driving unit include a large movement mode and a small movement mode, and when the infusion is performed, the driving unit can switch between the large movement mode and the small movement mode to realize increment-adjustable infusion.

According to an aspect of the invention, the plurality of movement modes of the driving unit further include one or more intermediate movement modes, wherein the intermediate movement mode is between the large movement mode and the small movement mode, and the driving unit can switch among the large movement mode, the intermediate movement mode and the small movement mode to achieve increment-adjustable infusion.

Compared with the prior art, the technical solution of the present invention has the following advantages:

In the drug infusion device disclosed by the present invention, the driving unit includes more than two driving arms, the driving unit, through the adjustable pivoting movements, drives driving arms to perform tooth number adjustable driving on the driving wheel for increment-adjustable infusion. When more than two driving arms are installed on the driving unit, the driving unit cooperates with the driving wheel to realize adjustable rotation: the driving arm driving the driving wheel to rotate by an optional number of teeth, thereby realizing increment-adjustable infusion of drug, which makes the infusion process more flexible and controllable and significantly improves the efficiency of drug infusion. At the same time, it also reduces the minimum drug infusion amount, accurately controls the process of the drug infusion, effectively avoids large fluctuations of concentration of some substance(s) in patient's body fluid and enables the patients to control and manage their physiological condition more precisely.

Furthermore, adjustable pivoting movements of the driving unit includes: after pivoting by an optional number of degrees in one direction in single time, the driving unit starts pivoting by an optional number of degrees in another direction until the end of the pivoting in this direction, the driving unit completes an alternate pivot in both directions. When a plurality of pivot modes are available, one of the pivot modes can be selected for the driving unit according to actual needs, driving the driving wheel to rotate by an optional number of teeth, thereby realizing the increment-adjustable infusion of the device, and allowing the patient to control the infusion process more flexibly.

Furthermore, a plurality of driving arms are installed on each side of the driving unit. Multiple driving arms on both sides can better achieve adjustable pivot of the driving unit.

Furthermore, in the solution of the present invention, when driving arms on one side of the driving unit engage the teeth, the plurality of driving arms on this side intersect in a line in which the engaging direction is located. Since the circumferential surface of the driving wheel has a circular arc shape as a whole, the engaged tooth faces of the adjacent gear teeth are not parallel to each other, and the intersection of the plurality of driving arms on one side in engaging direction can ensure the engaging direction is perpendicular to the tooth engaging surface, which improves the efficiency of engaging.

Furthermore, in the solution of the present invention, the teeth are ratchet teeth. Using of ratchet teeth can effectively prevent the driving wheel from being reversed cooperating with the driving arms. In addition, during the whole process of the driving unit pivoting in one direction, the driving unit alternately pivots and stops in an adjustable way to drive the driving arms to alternately engage and stop engaging the ratchet teeth, so that the driving wheel alternately rotates and stops rotation to perform tooth number adjustable driving on the driving wheel. In a single rotation in one direction, the driving unit's adjustable pivoting helps delivering the infused drug in several steps by means of a pivot-stop-pivot-stop-. . . alternating method to achieve accurate infusion.

Furthermore, multiple-gear positions of the driving unit include large gear position and small gear position. Patients can freely choose and switch large gear position or small gear position infusion according to the actual infusion volume and infusion rate requirements, making the infusion process more flexible and controllable, greatly improving the infusion efficiency.

Furthermore, a plurality of movement modes of the driving unit further include one or more intermediate movement modes. Setting intermediate movement modes provides more infusion options for the patient and the patient's control of the infusion process is more flexible.

DESCRIPTION OF THE EMBODIMENTS

Figure 1:
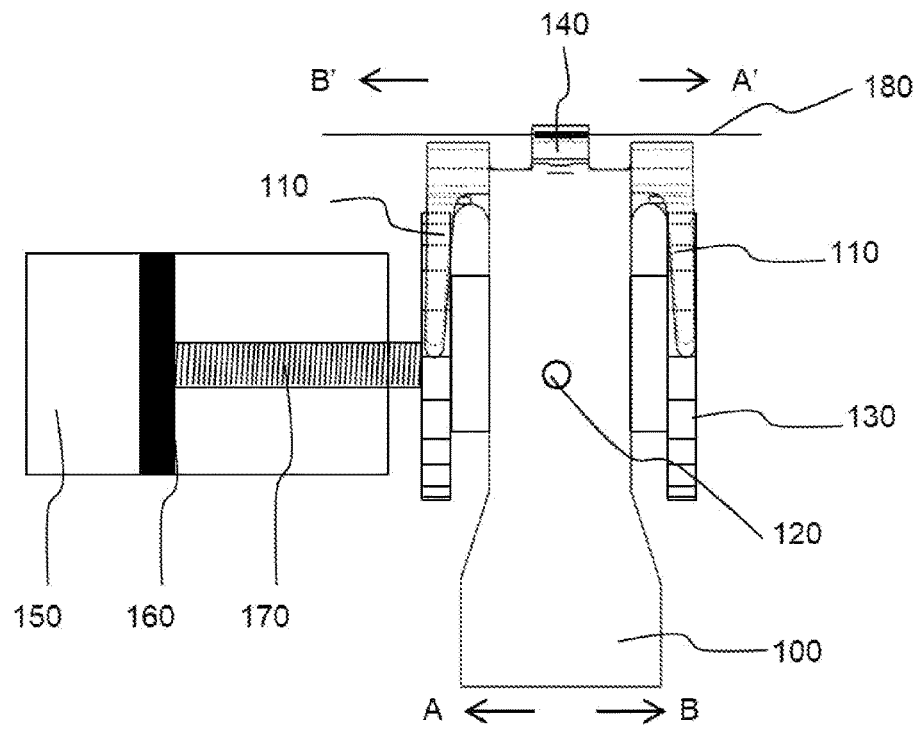
FIG. 1 is a top view showing structure of a drug storage unit, a piston, a screw, a driving unit, a power unit, and a driving wheel in a drug infusion device according to an embodiment of the present invention.

As previously mentioned, prior art infusion devices have only one un-adjustable infusion mode and do not have the flexibility to control the infusion process.

It has been found through research that the above mentioned problems are caused by the fact that the prior art drug infusion device can only drive the driving wheel to rotate in an unadjustable way, and cannot repeat the rotate-stop process for multiple times in a single period, which results in a relatively simple control of the infusion process in the prior art.

In order to solve this problem, the present invention provides a drug infusion device in which a driving unit is pivoted in an adjustable way to perform tooth-number adjustable driving on the driving wheel. The different options of increment allow patients to flexibly control the drug infusion process. At the same time, the minimum drug infusion amount of the infusion device is effectively reduced, and the fluctuation of concentration of some substance(s) in patient's body fluid is mitigated.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

FIG. 1 is a top view showing the structure of a drug infusion device according to an embodiment of the present invention. The drug infusion device includes a driving unit 100, a driving wheel 130, a drug storage unit 150, a piston 160, a screw 170, and a power unit 180.

The screw 170 is coupled to the piston 160 and the driving wheel 130, respectively. In the embodiment of the present invention, the driving wheel 130 is movably mounted on the device base (not shown), and the driving wheel 130 moves the driving screw 170 through rotation to advance the piston 160 disposed in the drug storage unit 150 to move forward for the purpose of injecting drugs.

The driving unit 100 is used to drive the driving wheel 130 to rotate. The driving unit 100 is movably connected to the device base through the pivot shaft 120. The power unit 180 is used to apply a force to the driving unit 100 to lead the driving unit 100 pivot. In the embodiment of the present invention, the power unit 180 is fixedly connected at the top position of the driving unit 100, thereby dividing the power unit 180 into two left and right portions, such as the A' direction portion and the B' direction portion in FIG. 1. The driving unit 100 is alternately led to pivot in the A' direction or the B' direction through the pivot shaft 120. Specifically, in the embodiment of the present invention, when the power unit 180 leads the driving unit 100 in the A' direction, the driving unit 100 pivots in the A direction through the pivot shaft 120. When the power unit 180 leads the driving unit 100 in the B' direction, the driving unit 100 pivots in the B direction through the pivot shaft 120. By alternately leading the driving unit 100 in the A' direction and the B' direction, the driving unit 100 can be alternately pivoted through the pivot shaft 120 in the A direction and the B direction.

Specifically, in the embodiment of the present invention, the power unit 180 is a shape memory alloy. The A' direction portion and the B' direction portion of the shape memory alloy are alternately powered on and off, and a leading force is applied to the driving unit 100 by a change in the length of the power unit 180 thereof. The power unit 180 may be composed of one piece of shape memory alloy, or may be composed of left and right segments (such as the A' direction segment and the B' direction segment) of shape memory alloy, and is not specifically limited herein, as long as the force can be applied to lead the driving unit 100 pivot.

Here, it should be noted that the power unit 180 includes but is not limited to a shape memory alloy. In other embodiments of the present invention, the power unit 180 may also be other structures, and the location where the power unit 180 applies force to the driving unit 100 is also not limited to the top position 140, as long as the action of applying a force to the driving unit 100 can be satisfied to cause the driving unit 100 to alternately pivot left and right.

Figure 2A:
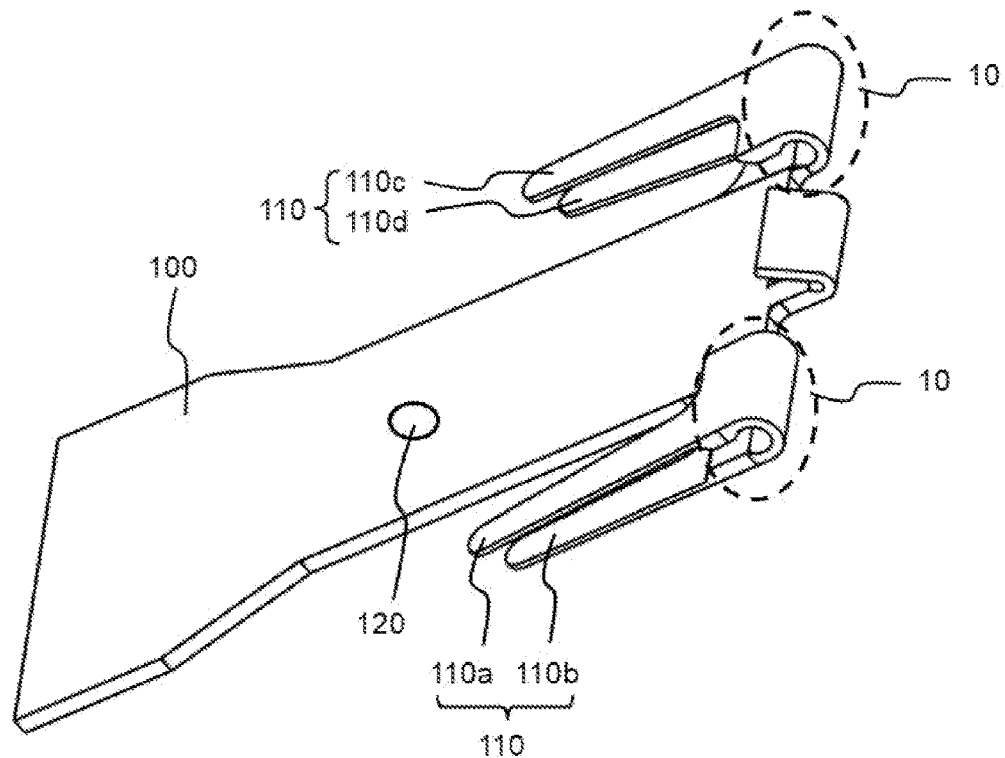
FIG. 2a-FIG. 2c are respectively a perspective view of a three-dimensional structure, a side view and a top view of a driving unit in a drug infusion device according to an embodiment of the present invention.
Figure 6:
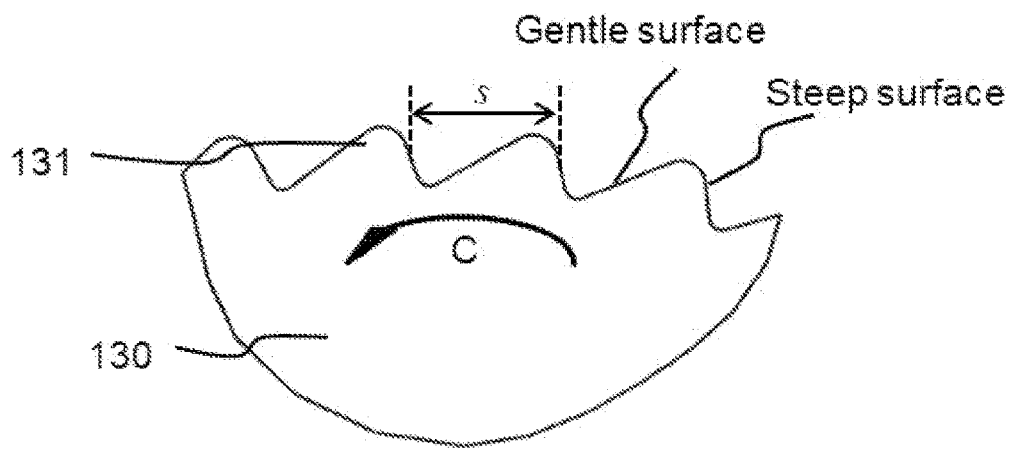
FIG. 6 is a partial structural view of a driving wheel in a drug infusion device according to an embodiment of the present invention.
Figure 7:
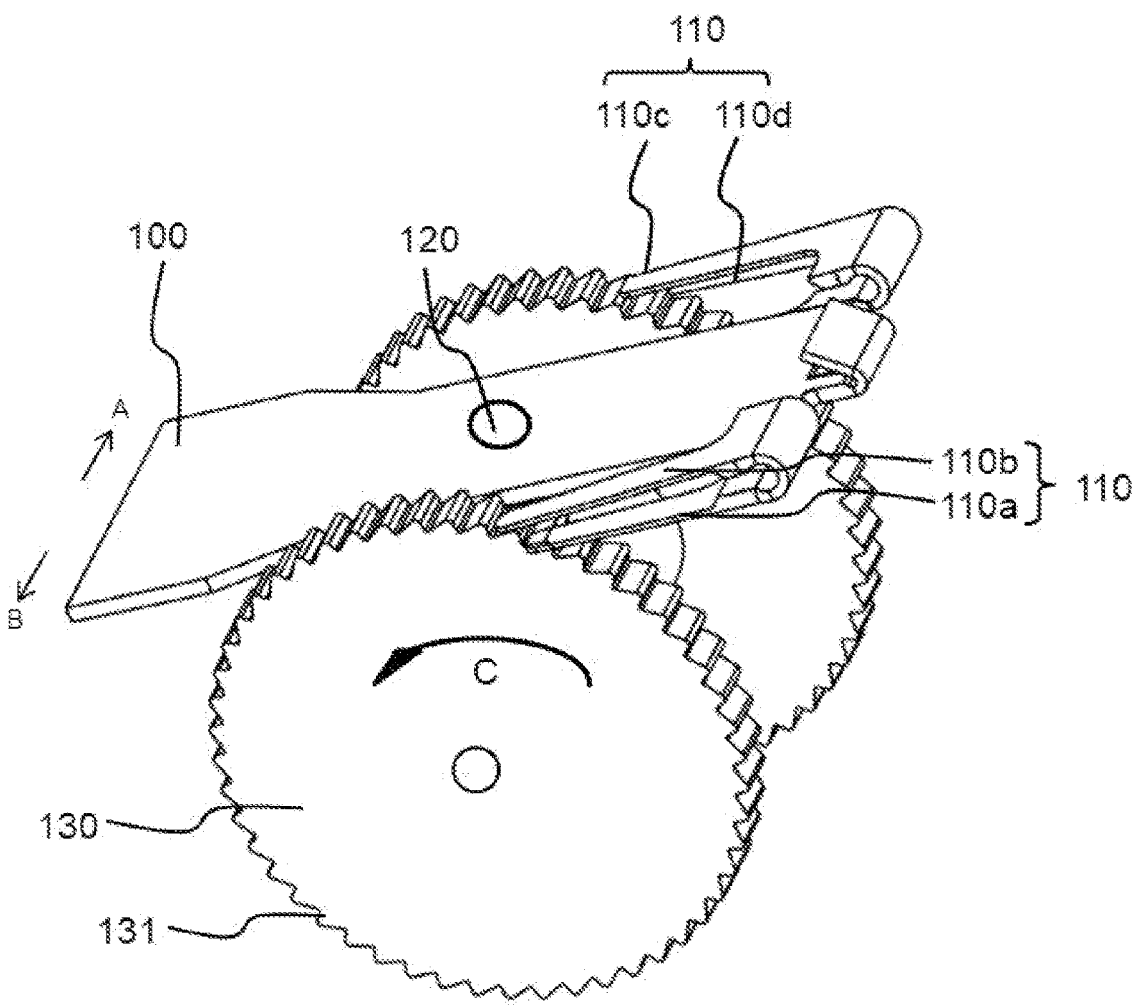
FIG. 7 is a schematic structural view of a driving unit pushing a driving wheel in a drug infusion device according to an embodiment of the present invention.

Referring to the perspective view of the driving unit 100 shown in FIG. 2a, the driving unit 100 further includes more than two driving arms 110. The driving wheel 130 includes a plurality of sub-wheels, and the circumferential surface of the sub-wheels is provided with gear teeth 131 (as shown in FIG. 6 and FIG. 7 below). Referring to the structure shown in FIG. 1 and FIG. 2a, when a plurality of driving arms 110 are installed on one side of the driving unit 100, the driving unit 100 can drive the driving arms 110 to engage the gear teeth 131 through adjustable pivoting to rotate the driving wheel 130 by an optional number of teeth. Thus, in an embodiment of the invention, driving unit 100 and driving wheel 130 are designed to work compatibly, which means that the position of the driving wheel 130 and the number of the sub-wheels need to be compatible with the working principle of the driving unit 100 and the number, position and structure of the driving arms 110.

As shown in FIG. 1 and FIG. 2a, in the embodiment of the present invention, a plurality of driving arms 110 are installed on each side of the driving unit 100. Therefore, a plurality of sub-wheels are also installed on both sides of the driving unit 100 to cooperate with the driving arms 110. Specifically, in the embodiment of the present invention, the driving unit 100 includes four driving arms 110, which are 110a, 110b, 110c, and 110d, respectively. 110a, 110b are installed on one side of the driving unit 100, while 110c, 110d are installed on the other side of the driving unit 100. The driving wheel 130 includes two sub-wheels, one of which cooperates with 110a, 110b and the other of which cooperates with 110c, 110d.

It should be noted that the driving wheel 130 may further include more than two sub-wheels. For example, according to the design of the position and structure of the plurality of driving arms 110, two adjacent sub-wheels may be set on one side of the driving unit 100 to cooperate with different positions, numbers of driving arms 110 on this side of the driving unit 100.

Figure 2B:
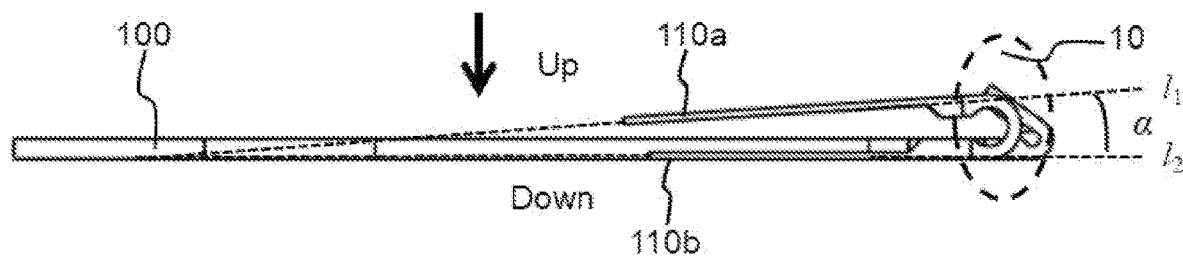
Figure 2C:
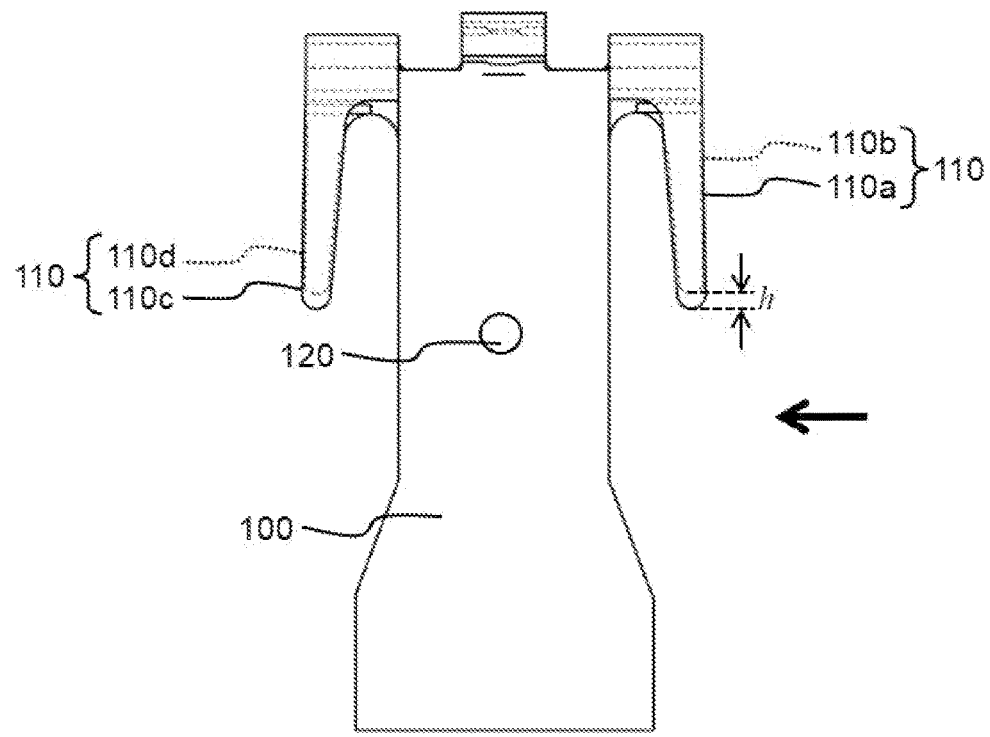

FIG. 2a, FIG. 2b, and FIG. 2c are respectively a schematic view of a three-dimensional, a side view, and a top view of the driving unit 100, and the top view direction of FIG. 2c is the direction indicated by the arrow in FIG. 2b, while the side view direction of FIG. 2b is the direction shown by the arrow in FIG. 2c.

In the embodiment of the present invention, the two driving arms 110 on one side of the driving unit 100 are installed up and down. Here, the up and down settings refer to the up and down positional relationship representations shown in FIG. 2b. Specifically, the two driving arms 110 (such as 110a and 110b) on the side of the driving unit 100 can be seen in the side view FIG. 2b, and in the top view FIGS. 2c, 110b and 110d are blocked by 110a and 110c, respectively, wherein 110b and 110d are indicated by dotted lines in FIG. 2c.

In the embodiment of the present invention, since the driving wheel 130 is circular, the surfaces on which the adjacent teeth are applied with the engaging force are not parallel. Therefore, in order to keep the angle between the driving arms 110 and the teeth engaging surface 90 degree during engaging, thereby improving the engaging efficiency of the driving arms 110, when the driving arms 110 on one side of the driving unit 100 engage the gear teeth 131, the lines representing the engaging directions of the two driving arms 110 intersect each other. Specifically, as shown in FIG. 2b, when the gear teeth 131 are engaged by 110a and/or 110b, the straight line where 110a is located is l1, the straight line where 110b is located is l2, wherein the angle between l1 and l2 is $\alpha$, $3.1° \leq \alpha \leq 4.1°$. Specifically, in the embodiment of the present invention, $\alpha = 3.5°$. In another embodiment of the invention, $\alpha = 3.3°$. In still another embodiment of the invention, $\alpha = 3.9°$.

It should be noted that, in other embodiments of the present invention, according to different structural designs, when the driving arms 110 on one side of the driving unit 100 engage the gear teeth 131, the lines representing the engaging directions of these two driving arms 110 can also be parallel (α=0°) or skew with a structure also able to drive the driving wheel 130 to rotate to achieve the purpose of drug infusion. In this case, the angle α between 11 and 12 may be set according to the actual structure, such as according to the diameter, number of the driving wheels 130, the number of the gear teeth 131, the pitch of the screw 170, the positional relationship and the number of the driving arms 110. For example, α may be between 0°~3.1° or 4.1°≤α≤7°, and is not specifically limited herein.

Figure 3A:
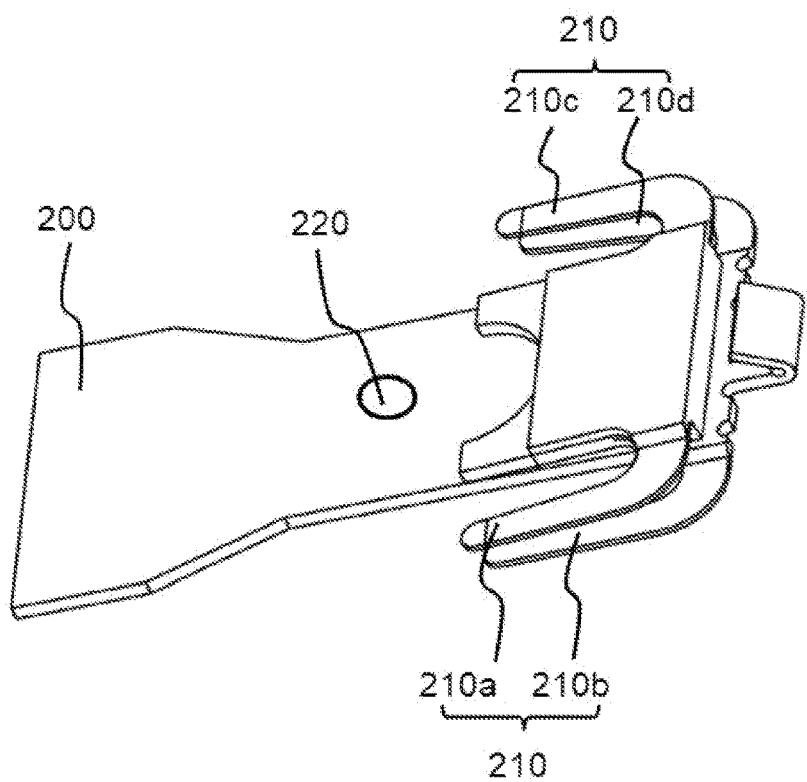
FIG. 3a-FIG. 3b are a schematic perspective view of a driving unit of a drug infusion device according to another embodiment of the present invention.
Figure 3B:
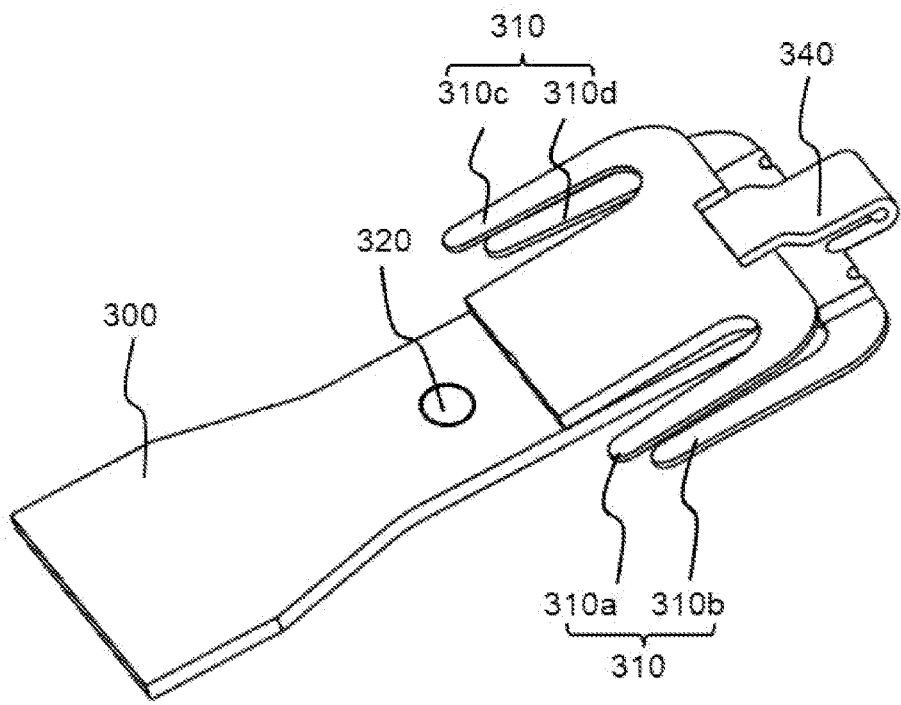

As shown in the dotted portion 10 of FIG. 2a and FIG. 2b, in the embodiment of the present invention, the two driving arms 110 on one side of the driving unit 100 are formed by folding at the dotted circle 10. In other embodiments of the present invention, the two driving arms 110 on one side of the driving unit 100 may also be formed by other means. As shown in the perspective view of the driving unit 200, 300 shown in FIG. 3a and FIG. 3b, the up position 210a, 210c, 310a, 310c and the down position 210b, 210d, 310b, 310d are respectively set in different structural subunits. As in FIG. 3a, the two structural subunits are secured together by welding or other means of attachment to form one single structure. And as shown in FIG. 3b, the two structural subunits are connected at the top position 340 of the driving unit 300, and then the top position 340 of the driving unit 300 is folded over to form the structure of the driving arms 310 in the embodiment of the present invention. In addition, the driving units 200, 300 pivot around the pivot shafts 220, 320, respectively.

It should be noted that, in other embodiments of the present invention, the driving arms may be formed by other means, as long as the arms are able to drive the driving wheel to rotate, and is not specifically limited herein.

Figure 4:
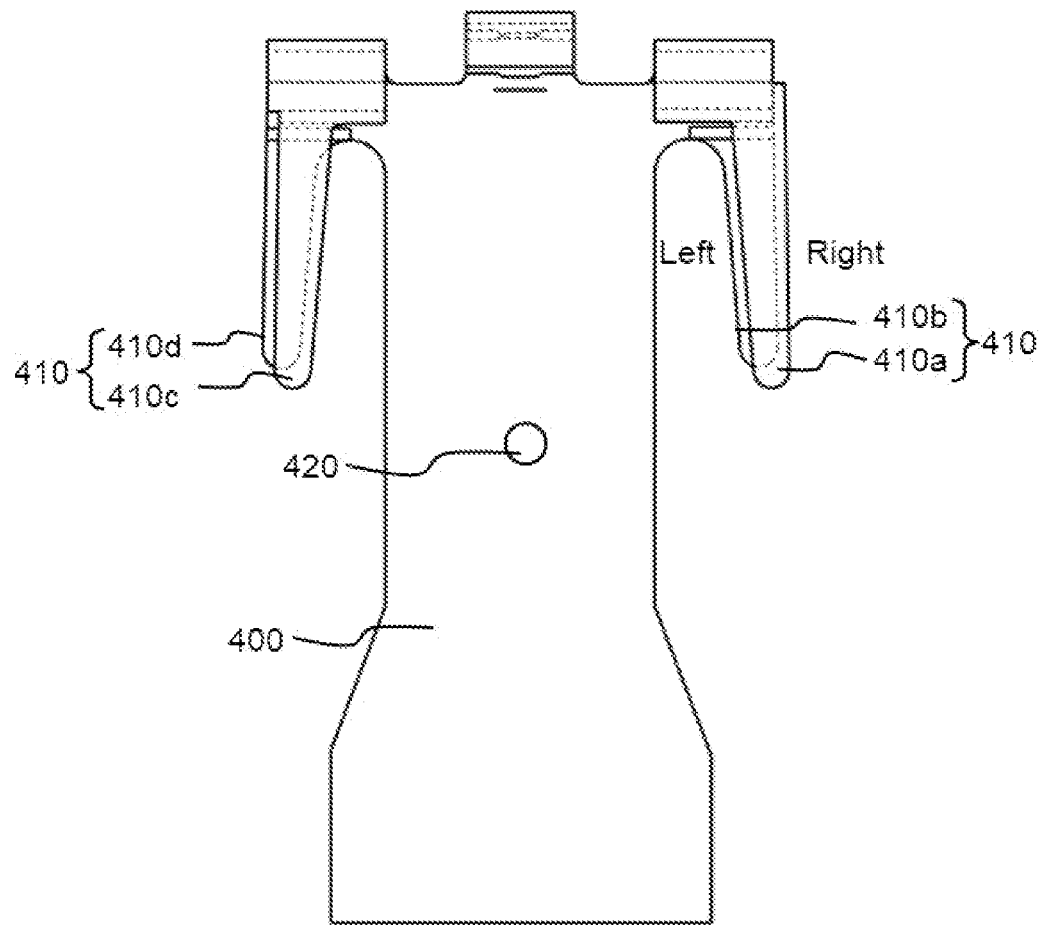
FIG. 4 is a perspective view showing the structure of a driving unit in a drug infusion device according to another embodiment of the present invention.

Please refer to FIG. 4, which is a top view of a driving unit 400 according to another embodiment of the present invention. In addition, the driving unit 400 pivots around pivot shaft 420.

The angles of view of FIG. 4 and FIG. 2c are the same. According to FIG. 2a, FIG. 2b, FIG. 2c and FIG. 4, it is apparent that the two driving arms on one side of the driving unit 400 are slightly offset from left and right, such as 410a, 410b and 410c, 410d. Specifically, in one embodiment of the invention, 410a and 410c are offset to the right and 410b and 410d are offset to the left.

It should be noted that, in other embodiments of the present invention, the left and right offset degree of the two driving arms on the same side and the direction in which the two are offset relative to each other need to be determined according to the actual structural design, and are not limited specifically described herein. Furthermore, in an embodiment of the invention, the two driving arms on one side of the driving unit can also be installed left and right. Here, the left and right installing mean that from the perspective of FIG. 4 (top view), two complete driving arms on one side of the driving unit can be seen, while from the perspective of FIG. 2b (side view), the driving arms close to the main body of the driving unit is completely or partially blocked by the driving arms away from driving unit's main body. In this case, the lines presenting the engaging directions of driving arms on the same side of driving unit is coplanar or skew. At the same time, there is no particular limitation on the length or the length relationship among different driving arms.

Figure 5:
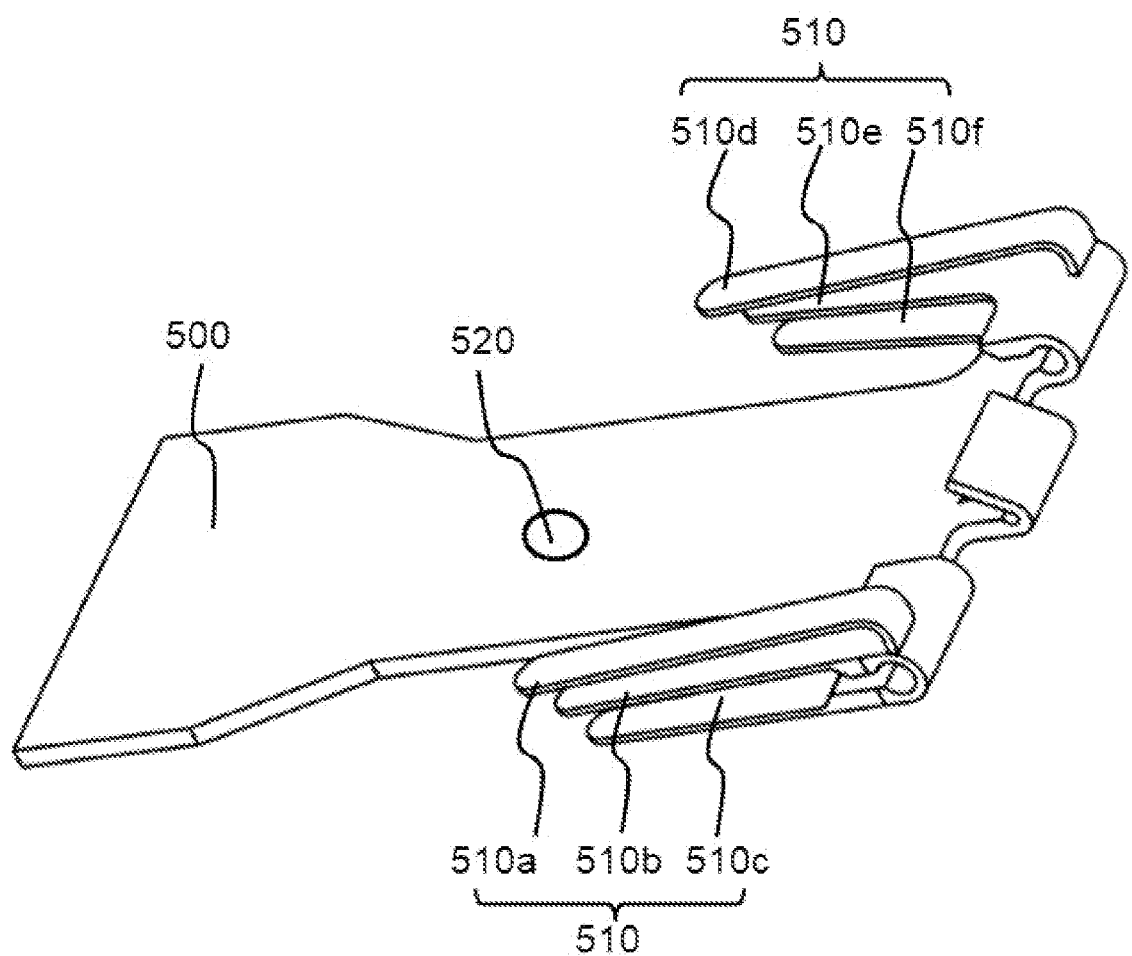
FIG. 5 is a perspective view showing the structure of a driving unit in a drug infusion device according to another embodiment of the present invention.

Please refer to FIG. 5, which is a schematic perspective view of a driving unit 500 according to still another embodiment of the present invention. In addition, the driving unit 500 pivots around pivot shaft 520.

Specifically, the driving unit 500 includes six driving arms 510, each three of which are installed on one side of the driving unit 500. Specifically, 510a, 510b, and 510c are installed on one side, and 510d, 510e, and 510f are installed on the other side. As described above, the lengths, the length relationships and the positional settings of the driving arms 510 on the same side are designed according to the specific structure and working principle, and are not specifically limited herein. Specifically, in the embodiment of the present invention, the positional relationship of the three driving arms 510 on the same side of the driving unit 500 is similar to that in FIG. 2a, FIG. 2b and FIG. 2c, that is, the three driving arms 510 on the same side of the driving unit 500 are installed up and down.

It should be noted that, in other embodiments of the present invention, the total number of driving arms may also be an odd number, such as three, five or more, that is, the numbers of driving arms on both sides of the driving unit are not equal. Moreover, the structural relationship between the different driving arms can be similar to that described above, and no specific restrictions are imposed here.

Referring to FIG. 6 and FIG. 2c together, FIG. 6 is a partial structural diagram of the driving wheel 130, and gear teeth 131.

In the perspective of FIG. 2c, the horizontal distance between the driving ends of the two driving arms on one side of the driving unit 100 is h, and the pitch of the gear teeth 131 is s, then 0.5 s≤h≤1.5 s. Specifically, in the embodiment of the present invention, h=0.8 s. In another embodiment of the invention, h=1.2 s. In still another embodiment of the invention, h=s. Here, the driving end of the driving arms 110 refers to the end of the driving arms 110 that directly contacts the gear teeth 131 when engaged. The horizontal distance refers to the plane distance between the driving ends of the two driving arms 110 on the same side of the driving unit 100 when viewed in an angle as shown in FIG. 2c.

It should be noted that in other embodiments of the present invention, 0.1 s≤h≤0.5 s or 1.5 s<h≤2.5 s may be used, and the effects of the present invention may be also achieved, and also are not specifically limited herein.

As shown in FIG. 6, in the embodiment of the present invention, the driving wheel 130 is a ratchet, and the gear teeth 131 are ratchet teeth. The use of a ratchet can prevent the driving wheel 130 from rotating reversely. Each ratchet tooth surface includes a gentle surface and a steep surface, as shown in FIG. 6. Moreover, in the embodiment of the present invention, the driving arms 110 of the driving unit 100 include a portion that drives the driving wheel 130 to rotate and a portion that does not drive the driving wheel 130 to rotate during the entire pivot of the driving unit 100 in one direction. The portion that drives the driving wheel 130 to rotate applies the engaging force on the steep surface of the ratchet teeth, in order to drive the driving wheel 130 to rotate in the C direction.

Please refer to FIG. 7, which is a schematic perspective view of the driving unit 100 and the driving wheel 130.

With reference to FIG. 7, FIG. 1, FIG. 2b and FIG. 2c, in the embodiment of the present invention, under the action of the power unit 180, the driving unit 100 pivots around the pivot shaft 120, thereby driving the plurality of driving arms 110 on both sides of the driving unit 100 to engage the gear teeth 131 for rotation of the driving wheel 130.

Figure 8:
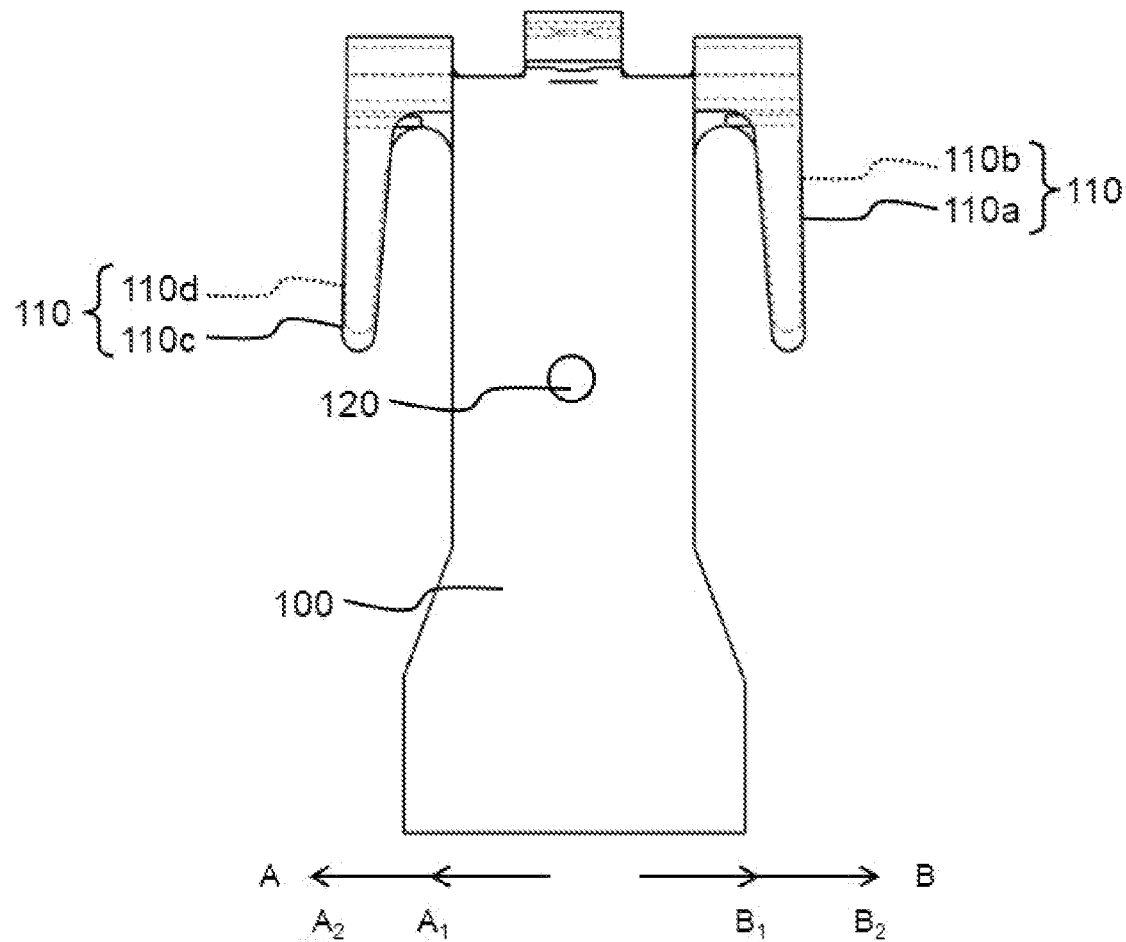
FIG. 8 is a schematic structural view showing a pivoting position of different movement modes of a driving unit in a drug infusion device according to an embodiment of the present invention.

Referring to FIG. 7 and FIG. 8 together, FIG. 8 is a schematic structural diagram of the adjustable pivoting movements of the driving unit 100.

As described above, the driving unit 100 has a certain distance h between the driving ends of the driving arms 110 on the same side, and there is a certain angle α between the lines representing the driving directions when the arms are engaged. And therefore, the driving unit 100 pivots in one direction in a single time throughout the process, as shown in FIG. 7 in a single pivot in the direction A, 110a and/or 110b engage the gear teeth 131 to drive the driving wheel 130, while 110c and 110d can slide on the gear teeth 131 (as on the gentle surface of the ratchet teeth, but not exert a force for driving the driving wheel 130 to rotate). And obviously, 110c slides to the next adjacent tooth first and makes a "click" sound. At this time, the driving end of 110c acts on the steep surface of the ratchet teeth to prevent the driving wheel 130 from being rotated reversely. At this time, the driving unit 100 stops pivoting and the driving arms 110a and/or 110b stop engaging the gear teeth 131, and the driving wheel 130 stops rotating. Thus the driving unit 100 completes one step of pivot. Referring to FIG. 8, the driving unit 100 pivots in the A direction to reach the A1 position. The next moment the driving unit 100 continues to pivot in the A direction, 110d will slide to the next adjacent tooth and will make another "click" sound. Similarly, the driving end of 110d also acts on the steep surface of the ratchet teeth to prevent the driving wheel 130 from rotating reversely. Thus the driving unit 100 completes a second step of pivot. Referring to FIG. 8, the driving unit 100 pivots to reach the A2 position. At this time, 110c and 110d respectively complete the sliding between adjacent gear teeth 131, and the driving unit 100 completes the whole process of single pivot in the A direction, reaching A1 and A2 positions respectively, thereby driving the driving wheel 130 to rotate by two steps, realizing two-step infusion of the drug device.

It should be noted that, in the above pivoting process, 110d may first slide to the next gear tooth 131, and then 110c slide to the next gear tooth 131, which is not specifically limited herein. Similarly, when the driving unit 100 pivots in the B direction, it can reach B1 and B2 positions respectively.

Obviously, in the whole process of the above-mentioned single pivot in the A direction, the driving unit 100 undergoes an alternate action of pivot and stop, and the driving arms 110 alternately engage and stop engaging gear teeth 131 to drive the driving wheel 130 to rotate and stop rotating, realizing two-step rotation of the driving wheel, and finally achieves two-level increment-adjustable drug infusion.

Specifically, when the driving unit 100 has two driving arms 110 on one side, the driving unit 100 undergoes two-step movement of the pivot-stop-pivot-stop during the single pivot in the A direction, in order to drive driving wheel 130 for two-step rotation. When the driving unit 100 has three driving arms 110 on one side, the driving unit 100 performs the pivot-stop-pivot-stop-pivot-stop three-step motion in the whole process of single pivot in the A direction, realizing three-step rotation of the driving wheel 130 to achieve three-level increment-adjustable drug infusion. By analogy, when there are more driving arms 110 on one side of the driving unit 100, the driving unit 100 realizes multiple-step driving of the driving wheel 130 by the multiple-step actions of the pivot-stop-pivot-stop-pivot- . . . -pivot-stop, completing multi-level increment-adjustable drug infusion.

With continued reference to FIG. 7, in combination with the above, in the embodiment of the present invention, when the driving unit 100 drives the driving wheel 130 to rotate, at least one of the driving arms 110 on the driving force side applies an engaging force to the gear teeth 131. While one or both of the driving arms 110 on the other side are in contact with the gear teeth 131 without applying any force to the gear teeth 131 to drive the driving wheel 130 to rotate, only applying a force if necessary for preventing the driving wheel 130 from being reversed. Therefore, there is a case in the embodiment of the present invention that only one of the driving arms 110 of the driving unit 100 applies a force to the gear teeth 131 to push the driving wheel 130 to rotate, and the other driving arms 110 are in contact with the driving wheel 130 without applying any force to the gear teeth 131 to drive the rotation of the driving wheel 130. At this time, the driving arm 110 that slides on the teeth on the other side applies a force to the gear teeth 131 to prevent the driving wheel 130 from being reversed.

It should be noted that, in the embodiment of the present invention having three or more driving arms 110 on one side of the driving unit 100, when the driving unit 100 is in operation, the above-mentioned similar situation may also occur. When there are an odd number of driving arms, the numbers of driving arms on both sides of the driving unit are not equal, and the same process as above is also performed in the whole process of the driving unit rotating in a certain direction.

Referring to FIG. 8 again, in another embodiment of the present invention, when the driving unit 100 has two driving arms 110 on one side, the driving unit 100 pivots one step in the A direction, that is, reaching the A1 position, and then pivots one or two steps in the B direction, that is, reaching the B1 or B2 position until the pivot in the B direction stops. This process completes the alternate pivot of the driving unit 100 in two directions, so that the driving wheel 130 can be rotated in multiple steps. Therefore, in the embodiment of the present invention, the driving unit 100 can alternately switch modes among A1-B1 or A1-B1-B2 or B1-A1-A2, so as to achieve the purpose of switching among different increments of infusion.

With continued reference to FIG. 8, in another embodiment of the present invention, the driving unit 100 can also be pivoted directly to the A2 position without passing through the A1 position, then directly pivoted to the B2 position without passing through the B1 position, that is, the driving unit 100 alternately pivots between the A2-B2 positions. As described above, the driving unit 100 can also alternately pivot between the A1-B1 positions. Obviously, in a unit time, the dose of infused drug when the driving unit 100 alternately pivots between the A2-B2 positions is greater than the dose of infused drug when it alternately pivots between the A1-B1 positions. If the minimum dose of infused drug driven by the driving unit is the minimum increment of the infusion device, the drug infusion device using the embodiment of the present invention can reduce the minimum increment of drug dose and achieve more precise control of the drug infusion. When the patient needs to infuse more drugs, the large A2-B2 mode can be selected to speed up the infusion rate. When a small amount of drug needs to be infused, the patient can select the small A1-B1 mode to reduce the drug infusion rate and achieve precise control of the drug infusion.

In a drug infusion system, only one driving arm is set on each side of the driving unit, and only one-step rotation of the driving wheel can be performed in the whole process of rotating in one direction, that is, driving unit alternately moving between A2-B2 as shown in FIG. 8. This one-level driving method does not provide flexibility in controlling drug dose and infusion rate. At the same time, the minimum dose of infused drug is large, and it is hard to accurately control the drug infusion, which will eventually lead to a large fluctuation in the concentration of some substance(s) in a patient's body fluid. And it is also a waste of drugs and increasing the cost for patients.

Compared with the device with increment-unadjustable infusion, the drug infusion device of the embodiment of the invention realizes driving degree-adjustable rotation of the driving wheel by setting more than two driving arms on the driving unit, thereby achieving increment-adjustable drug delivery. With the drug infusion device of the embodiment of the invention, the patient can freely and flexibly switch between different increments of infusion according to the actual drug dose and the demand of the infusion rate, thereby improving the infusion efficiency. At the same time, intermediate A1-B1-B2 mode or B1-A1-A2 mode and the small A1-B1 mode are set along with the large A2-B2 mode. And the drug infusion device can reduce the minimum dose of infused drug in order to achieve the goal of precise control of the infusion.

As with the drug infusion device of the embodiment of the present invention, when the infusion is started, the amount of drug required is relatively large, and the patient can select the large A2-B2 position shown in FIG. 8 for infusion. After a period of infusion, the intermediate A1-B1-B2 mode or B1-A1-A2 mode can be used to reduce the rate of drug infusion. When the drug infusion is about to be completed, the patient can switch to the small A1-B1 mode to further reduce the infusion rate and achieve precise control of the drug infusion. Of course, the patient can also choose one or several of the modes for infusion, and there are no specific restrictions.

In other embodiments of the present invention, when more than two driving arms 110 are installed on one side of the driving unit 100, the drug infusion device can have more and more elaborate infusion modes, and the patient can further flexibly control the infusion to make the infusion process more precisely.

In summary, the present invention discloses a drug infusion device, in which more than two driving arms are installed on a driving unit, and the driving unit drives the driving wheel to rotate by an optional number of teeth through different pivoting movement modes, thereby realizing increment-adjustable drug infusion, increasing the patient's flexibility in controlling the infusion process and improving the efficiency of drug infusion. At the same time, the drug infusion device also reduces the minimum dose of infused drug, from which the patients can accurately control the drug infusion and precisely manage their own physiological condition.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

What is claimed is:

1. An infusion device, comprising:
  a drug storage unit;
  a screw, a piston and a driving wheel respectively connected with the screw, the driving wheel drives the screw to move by rotation, the piston is arranged in the drug storage unit, the screw advances the piston to move;
  a driving unit cooperating with the driving wheel, the driving unit comprises more than two driving arms which drive the driving wheel to rotate, the driving unit, through multiple-mode pivot, drives the driving arms to perform a driving mechanism that uses any number of teeth and is adjustable on the driving wheel for increment-adjustable infusion; and
  a power unit connected to the driving unit, the power unit exerts a force on the driving unit to lead the driving unit to perform multiple-mode pivot,
  wherein the driving arms are respectively installed on two sides of the driving unit, each of the two sides of the driving unit is installed with two driving arms of the driving arms, distances between the two driving arms on each side of the driving unit become smaller along a direction towards two driving ends of the two driving arms, wherein the two driving ends of the two driving arms contact the driving wheel,
  wherein the multiple-mode pivot of the driving unit includes:
  after pivoting one or more steps in one direction in a single time, the driving unit starts pivoting one or more steps in another direction until an end of the pivot in this direction, the driving unit completes an alternating pivot in both directions to perform multiple-mode driving on the driving wheel.

2. The drug infusion device according to claim 1, wherein the driving wheel includes:
  a plurality of sub-wheels, a circumferential surface of each of the plurality of sub-wheels is provided with gear teeth, and the driving arms drive the driving wheel by engaging the gear teeth.

3. The drug infusion device according to claim 2, wherein when the driving arms on one side of the two sides of the driving unit engage the gear teeth of the driving wheel, lines representing engaging directions of the driving arms each occurring on the one side of the two sides intersect each other, and the engaging directions are directions that the two driving arms are oriented in when engaged with the gear teeth, respectively.

4. The drug infusion device according to claim 3, wherein the two driving arms on each of the two sides of the driving unit are oriented along a first direction, or are oriented along a second direction, the first direction is not parallel to the second direction.

5. The drug infusion device according to claim 4, wherein the two driving arms on each of the two sides of the driving unit are oriented along the first direction, and when the two driving arms on each of the two sides of the driving unit engage the gear teeth of the driving wheel, an angle between the lines representing driving directions of the two driving arms is $\alpha$, $0°\leq\alpha\leq7°$, the driving directions are directions that the driving arms are oriented in when driving the gear teeth, respectively.

6. The drug infusion device according to claim 5, wherein $3.1°\leq\alpha\leq4.1°$.

7. The drug infusion device according to claim 6, wherein $\alpha=3.5°$.

8. The drug infusion device according to claim 4, wherein a horizontal distance between driving ends of the two driving arms on the one side of the two sides of the driving unit is h, a pitch of the gear teeth of the driving wheel is s, $0.1s\leq h\leq2.5s$.

9. The drug infusion device according to claim 8, wherein 0.5s≤h≤1.5s.

10. The drug infusion device according to claim 2, wherein the gear teeth of the driving wheel are ratchet teeth, and during a whole process of the driving unit pivoting in either of the one direction or the another direction, the driving unit alternately pivots and stops multiple times to drive the driving arms to alternately engage and stop engaging the ratchet teeth, so that the driving wheel alternately rotates and stops rotation to perform the driving mechanism.

11. The drug infusion device according to claim 10, wherein
when the driving unit drives the driving wheel, at least one of the driving arms on one side of the two sides on which a driving force is applied engages the ratchet teeth of the driving wheel, and the driving arms on the other side of the two sides of the driving unit do not apply a force to the ratchet teeth of the driving wheel to rotate the driving wheel.

12. The drug infusion device according to claim 1, wherein the multiple-mode pivot of the driving unit comprises:
a large movement mode and a small movement mode, and when an infusion is performed, the driving unit switches between the large movement mode and the small movement mode to realize the increment-adjustable infusion.

13. The drug infusion device according to claim 12, wherein the multiple-mode pivot of the driving unit further comprises:
at least one intermediate movement mode, wherein the at least one intermediate movement mode is between the large movement mode and the small movement mode, and the driving unit switches among the large movement mode, the at least one intermediate movement mode and the small movement mode to achieve the increment-adjustable infusion.

* * * * *